United States Patent [19]
Ollivier

[11] Patent Number: 5,800,499
[45] Date of Patent: Sep. 1, 1998

[54] PROBE FOR AN IMPLANTABLE MEDICAL DEVICE

[75] Inventor: Jean-Francois Ollivier, Guyancourt, France

[73] Assignee: ELA Medical S.A., Montrouge, France

[21] Appl. No.: 770,794

[22] Filed: Dec. 20, 1996

[30]  Foreign Application Priority Data

Dec. 29, 1995 [FR] France .................. 95 15760

[51] Int. Cl.⁶ ......................................... A61N 1/05
[52] U.S. Cl. ............................... 607/126; 600/375
[58] Field of Search ........................... 128/642; 607/122, 607/126, 128, 116; 600/373, 374, 375

[56]  References Cited

U.S. PATENT DOCUMENTS

| | | | |
|---|---|---|---|
| 4,419,819 | 12/1983 | Dickhudt et al. | 29/857 |
| 4,564,023 | 1/1986 | Hess | 607/126 |
| 4,669,488 | 6/1987 | Hess | 607/126 |
| 4,913,164 | 4/1990 | Greene et al. | |
| 4,917,106 | 4/1990 | Oliver . | |
| 4,957,118 | 9/1990 | Erlebacher . | |
| 5,383,924 | 1/1995 | Brehier | 607/126 |

FOREIGN PATENT DOCUMENTS

| | | | |
|---|---|---|---|
| 0126892 | 12/1984 | European Pat. Off. | 607/126 |
| 0546414A1 | 6/1993 | European Pat. Off. | |
| 0573334A1 | 12/1993 | European Pat. Off. | |
| 3415410 | 10/1984 | Germany | 607/128 |

*Primary Examiner*—Jeffrey R. Jastrzab
*Attorney, Agent, or Firm*—Orrick, Herrington & Sutcliffe

[57]  ABSTRACT

A probe for an implanted medical device, more particularly for a cardiac pacemaker. The probe (10) has at its extremity a cylindrical body (14) supporting one or more electrodes (18) and a means of anchorage (34) extending radially around the exterior. A deformable sleeve (24), made of a supple material, covers the cylindrical body and supports the anchorage means. The sleeve has one end (or part) (26) attached to the body at the distal extremity of the probe, and one part (28) that is free or unconnected to the body spreading proximally in relation to the attached part and supporting the anchorage means. The free part is essentially applied in a separable manner against the body on the aforementioned distal region. The material of the sleeve is chosen to permit a reversal of the sleeve, that is turning the sleeve inside-out, in response to a force (40) axially exerted in the distal direction on the anchorage means, such that the sleeve in the inside-out position has the free part with the anchoring means turned radially to the interior, and extends distally in relation to the attached part. The probe distal extremity thus has a low profile for easy explantation.

18 Claims, 1 Drawing Sheet

PROBE FOR AN IMPLANTABLE MEDICAL DEVICE

FIELD OF THE INVENTION

The present invention concerns probes for implanted medical devices, more particularly probes for cardiac pacemakers.

BACKGROUND OF THE INVENTION

Probes for implantable medical devices, and particularly endocardial probes for use with cardiac pacemakers, typically include a retention system secured to the distal extremity, near the stimulation electrode (or electrodes, in the case of a bipolar or multipolar probe). The retention system operates to retain the distal end of the probe, and hence the electrode, in place against the tissue. These retention systems are also referred to as anchorage systems.

Various retention or anchorage systems have been proposed and are known in the art. Many of these systems have protruding structures in form of hooks or "tines" that come to wedge themselves between and against the endocardial trabecula.

It can be advantageous to construct these anchorage systems in a manner that will permit, in case of need, an explantation (extraction) of the probe without risk of tearing either the trabecula or the fibrous tissues which are typically formed around the extremity of the probe.

The "passive" anchorage systems are typically constructed in a manner that the tines lodge themselves in place as the probe is implanted, as a result of the elasticity of the material of which the tines are constructed. Thus, the tines project away from the probe at an angle that inhibits the probe from moving in the reverse direction without some particular maneuver.

On certain occasions, it can become necessary to remove a probe that h as been implanted for several years. This occurs, for example, in the cases of an unacceptable elevation of the stimulation (pacing stimulus) threshold, an infection, or a probe that has become defective for bad insulation or a fracture of the conductor.

One known technique is to provide a mechanical actuator, as, for example, in U.S. Pat. No. 4,957,118. In this disclosure, the tines are initially withdrawn against the probe body during insertion of the probe, and are deployed by operating a coaxial stylet that is inserted in the probe at the time of the implantation. The stylet operation is by rotation, once the probe is positioned at the desired place, which causes the tines at the distal extremity to protrude to hold the probe in place. Then, to remove the probe, the stylet is operated in the reverse manner, whereupon the tines are withdrawn an d the probe can be extracted.

These probes are nevertheless relatively cumbersome in that the diameter of the distal body is larger than probes not having this feature because it is necessary to provide an axial canal to receive the stylet. Further, these probes are more complex structurally, and hence more expensive, due to t he mechanical articulation system of the folding and unfolding of tines. They also are more expensive and due to the tolerances that are necessary to insure cooperation between the mechanical system and the central axial canal of the probe.

To allow the explantation without risk of tearing the trabecula or fibrous growth tissues, it is proposed in DE -3146182 to connect between the tines an intermediate sail (webbing) in a manner to form a conical and continuous skirt, the entire assembly being constructed from an elastomer of silicone or polyurethane. In this structure, at the time of the withdrawal of the probe, the cone becomes inverted, and thus avoids tearing the tissues.

This probe presents, however, at least two disadvantages. In the first place, the conical skirt, by its form, substantially prevents the growth of the fibrosis over the distal end. As a result, over the long term, there is a less secure anchorage than in the case of isolated tines, that is tines that are not connected by a skirt or webbing of material. In the second place, the outside diameter of the probe remains relatively large due to the widened form of the skirt, at the implantation and the explantation. Further, once detached from the trabecula and fibrotic tissues, the spring effect of the skirt returns, with a resultant widening of the cone turned in the proximal direction and, therefore, in a state that does not facilitate the withdrawal of the probe through a vein. In view of the diameter, this passive probe construction obtains no particular advantage in relation to probes having the mechanical actuator of the tines, and therefore imposes the same limitations to the physician during the extraction of the probe through the venous system that existed during the installation of the probe.

In addition, the extraction of such a probe, typically results in some tearing of fibrous tissue, and entails an enlarged thickness in the distal extremity of the probe due to the presence of the fibrotic tissues, which are likely to form a mass or plug that becomes a considerable obstacle to the withdrawal.

OBJECTS AND SUMMARY OF THE INVENTION

It is, therefore, an object of the present invention to provide a probe having a passive anchorage system that can be installed without a mechanical actuator, presents a small diameter in the case of an extraction, has a simple structure that is inexpensive to manufacture, and allows an easy explantation without significant risk of damage to the endocardial cavity tissues and the venous walls.

Broadly, the present invention, is directed to a probe of the type having at its distal extremity a cylindrical body supporting one or more electrodes and an anchorage system, the anchorage system extending radially outward at the exterior of the distal extremity in the normal position during use. In accordance with the present invention, the probe comprises a deformable sleeve made of a supple (flexible) material surrounding the cylindrical-body. One end of the sleeve is attached to the cylindrical body preferably near or-at the distal extremity of the cylindrical body (the so-called "attached part"), and the other end is not attached to the cylindrical body (the so-called "free" end) such that there is a length of the sleeve between the attached part and the free end (the so-called "free part") that is in contact with, but not secured to the cylindrical body. The sleeve also supports the anchorage system.

When the free end is most proximal in relation to the attached part, the sleeve is coaxial to and in contact with the cylindrical body of the probe, and the anchorage system extends radially at its normal position and in its normal configuration. The free part of the sleeve, however, is separable from the body of the probe. In this regard, the material of the sleeve is chosen in a manner to permit a reversal of the sleeve, that is a turning of the sleeve inside-out, in response to an axially exerted force or traction in the distal direction on the anchorage system. In such case, the sleeve in the reversed or inside-out position has the free part positioned distally in relation to the attached part, with the anchorage system now radially directed to the interior of the sleeve.

In a preferred embodiment, the inside-out position is a mechanically stable state, meaning that the sleeve will remain inside-out absent some specific force purposefully reversing the sleeve to its normal position. Further, the exposed surface of the sleeve in the inside-out state has an essentially smooth surface, without salient elements. This facilitates easy withdrawal of the probe.

Preferably, the anchorage system comprises a plurality of anchorage tines. More preferably, the sleeve and tines are constructed of a single molded element. The attached part of the sleeve can be the end of the sleeve, or a thickness at or near the end of the sleeve that is secured at or near the distal end of the cylindrical body. More preferably, the securement is by compressing a portion of the sleeve at its distal end between the electrode at the distal side of the attached part and a frontal face of the cylindrical body at the proximal side of the attached part. The compressed portion is even more preferably an annular protrusion of the sleeve having an increased thickness. Further, between the attached part and the free part of the sleeve may be a reduced thickness region, which reduced thickness operates as a hinge mechanism at the time of the reversal of the sleeve to the inside-out position. The reduced thickness portion is preferably located as close as possible to the attached part.

In one embodiment, the probe of the present invention advantageously provides an insulating sheath extending over at least a portion of the cylindrical body supporting the electrode, and the length of the free part of the sleeve in the proximal direction is preferably chosen in a manner that the sleeve will cover entirely the cylindrical body, and thus extend over the adjacent sheath, in tight contact with the former. It is therefore foreseen that a lubricating agent may be applied between the cylindrical body and the free part of the sleeve.

Preferably, the sleeve is made of radio-opaque material.

BRIEF DESCRIPTION OF THE DRAWINGS

Other features, characteristics and advantages of the invention will become more apparent to the person of ordinary skill in the art from the following detailed description of the invention, made with reference to drawings annexed, in which like reference numerals refer to like elements, and in which.

DETAILED DESCRIPTION OF THE DRAWINGS

Figure 1:
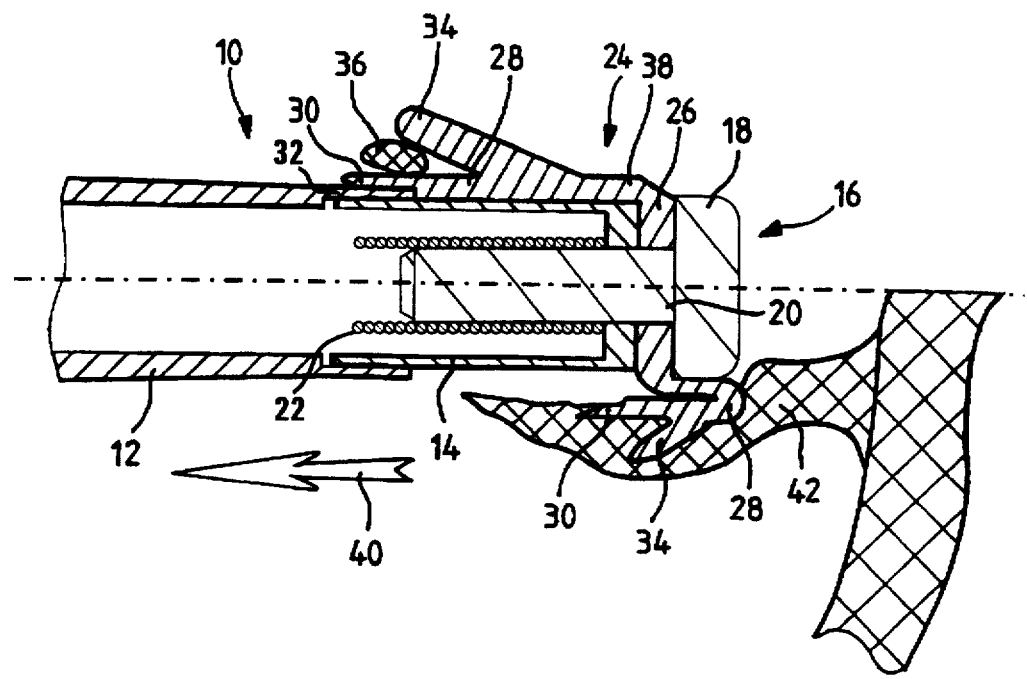
FIG. 1 is a cross-sectional view of the distal extremity of a probe according to a preferred embodiment of the present invention, the top half section showing the configuration of the distal probe extremity in its normal inserted and anchored position, and the bottom half section showing the configuration of the distal probe extremity at the beginning of a withdrawal phase.
Figure 2:
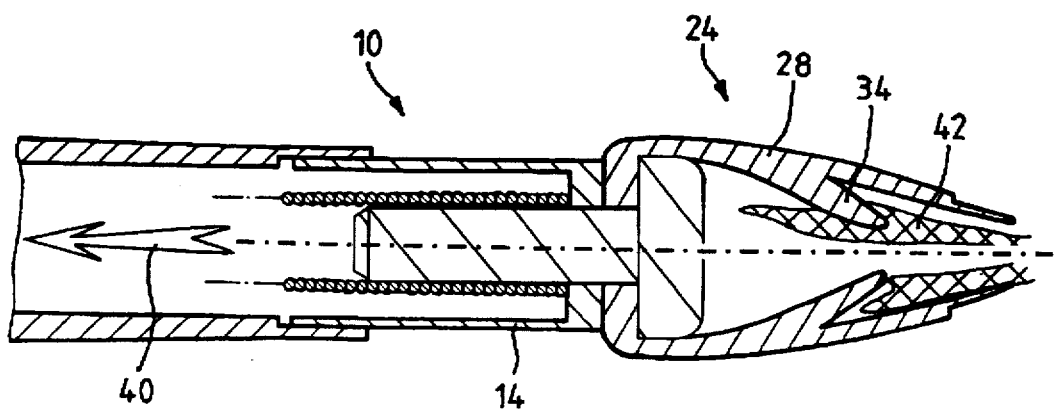
FIG. 2 is a cross-sectional view of the distal extremity of the probe of FIG. 1 later in the withdrawal phase, when the distal probe extremity detaches from the surrounding tissues.

With reference to FIGS. 1 and 2, the reference 10 designates, in a general manner, the distal extremity of a probe for an implantable medical device in accordance with the present invention. In the case of the illustrated example, the probe is a unipolar endocardial probe having a flexible insulating sheath 12 at the end of which is connected a rigid cylindrical body An electrode 16 is connected at the frontal face of body 14 (distal region). The electrode 16 typically comprises a flat head 18, which is designed to come into contact with the wall of the myocardium, and may be a standard or a carbonized tip electrode. Electrode 16 also has a stem 20 that extends inwardly of body 14 to be attached to a conductor 22. Conductor 22 is typically in the form of a spiral spring that extends inside and along sheath 12 to the proximal extremity of the probe, where conductor 22 is connected to the pacemaker (not shown). One suitable construction of the aforementioned elements of the probe is particularly comparable to that described in EP-A-0 296 001 in the name of the assignee of this invention ELA Medical and its corresponding U.S. Pat. No. 4,917,106, the latter of which is incorporated herein by reference in its entirety. It should be understood, however, that the present invention is applicable to virtually any probe for any implanted medical device, including cardiac pacemakers, cardioverters and defibrillators, which has an anchoring system.

In accordance with the present invention, the rigid cylindrical body 14 of probe is covered with a sleeve 24 that extends over the body, preferably over the entire length of body 14, so that it contacts sheath 12 in an overlapping relationship.

Sleeve 24 comprises, on the one hand, an annular part of attachment 26, which part 26 is captured (that is, compressed or pinched) between the distal face of the body 14 and the proximal side of flat part 18 of the electrode 16, and, on the other hand, a free part 28 covering the body 14. As previously noted, the term "free" means that part 26 is applied in contact against the body 14 of the probe, but is not attached, thereto, except for the attachment achieved in connection-with the annular part 26.

In the proximal direction, the free part 28 extends to the portion 30 which overlies and covers the distal extremity 32 of sheath 12. In this regard, the distal extremity 32 is pinched between, on the one hand, the body 14 and, on the other hand, the free part 30 of the sleeve 28. To avoid a bulge in the probe surface, that is an area of increased thickness due to an overlap, the distal extremity 32 of sheath 12 and/or the proximal extremity 30 of the sleeve 28 can be provided with a reduced thickness in the area of their superposition.

On the other hand, a certain tightness of fit can be obtained by a constriction of the diameter of the free part at its proximal extremity 30, with the result being that the free part adheres as much as possible to the body 14 and to the flexible sheath 12 to form a hermetic seal, or at least a seal having a certain degree of hermeticity. In this regard, there may be a silicone to silicone contact as between the sheath 12 and free part 28, when each is made of silicon. The constriction may be obtained by, for example, forming the free end with a smaller inner diameter relative to the body 14, that is to say it has a tighter fit that other parts of the free part.

The sleeve 28 supports, in a manner in itself known, a plurality of distinct anchorage tines 34. Tines 34 are salient, typically inclined in a proximal direction so that they will come to lodge between the trabecula 36 (one of which is so represented in FIG. 1) of the endocardial cavity when the probe is fully implanted, and tends to keep the probe fully inserted and prevent the probe from being inadvertently extracted. In addition, tines 34 tend over time to be enveloped by a fibrosis, and thereby anchor more firmly in place the distal extremity of probe due to the salient form of tines 34.

Advantageously, the region 38 which provides the transition between the free part 28 and the attached part 26 is a thinned region, that is a region of reduced thickness, in a manner to obtain an effect of a hinge between these two parts.

The sleeve 24 is made of a supple or flexible material, for example, a silicone elastomer, such as the product ETRQ7 47.80 having a Shore hardness in the range of from 30 to 80. Such a material presents a sufficient suppleness to permit the deformations that will be described below. The thickness of the free part of the sleeve may be from 0.5 to 1.0 mm., preferably 0.8 mm. The region of reduced thickness may be a reduction of from 30 to 70% of the thickness, as compared to the thickness immediately adjacent the thinned area. In considering the thickness of the sleeve, the additional material attributable to the anchorage system, whatever means for anchorage may be employed, should be effectively disregarded. The material should not, however, be too supple, because it has to be sturdy enough to resist bunching-up during repeated tests during the implantation phase, when the physician may move the probe forwards and backwards to realize the desired placement of the probe and overlapping of the tines in the trabecula. Stated otherwise) the sleeve should have sufficient rigidity-to resist turning inside-out when moving the probe to position the electrode in the desired location.

In operation, the probe of the present invention is introduced into a patient in the classic manner, which is comparable to that of a probe having a passive anchorage system (such as salient tines) of a known type. The advantage of the probe of the present invention appears at the moment of the definitive explantation. In this regard, when the physician exerts a traction force in the proximal direction (represented by arrow 40), the free part 28, which is restrained by the fibrosis 42 that has come to form around tines 34, is going to slip along the rigid body 14 of the probe and gradually separate therefrom, as illustrated on the lower half of FIG. 1.

This slipping can be advantageously facilitated by addition of a lubricating fluid or paste interposed between the external face of the body 14 and the internal face of the free part 28 of the sleeve 24. A suitable lubricant may be a medical grade silicone oil, available from Dow Corning.

The totality of these actions is going to provoke a bunching-up of the sleeve around the hinge zone 38, that leads to a folding over of the free part 28 of the sleeve 24 on to the attached part 26 With continued traction, as illustrated in FIG. 2, the free part 28 has turned inside-out and extends backwards (relative to the direction of the extraction), distally of the body 14, and tines 34 now project radially to the interior of the free part.

One will note that the inside-out position illustrated -in FIG. 2 constitutes a stable mechanical state, that-will allow the easy withdrawal of the probe in the venous circuit. The external surface of the inside out sleeve 28 has an essentially smooth exposed surface, since tines 34 are now turned to the interior.

At this stage of extraction, there are two likely possibilities. In the first case, the fibrosis will simply detach itself from the tines 34 and rest on the myocardium. The beginning of the process has, however, turned the sleeve inside out. Thus, the tines are directed to the interior and do not oppose or restrict the withdrawal of the probe through the veins. The result found is therefore the same configuration as one would have had with a smooth probe of a uniform diameter. The separation of tines 34 from the fibrosis 36 can be further facilitated by providing the tines with a slightly tapered form, that is to say the tine dimension in transverse section is smaller near the extremity than near the base.

In the second case, the fibrosis continues, partially or totally, to adhere to the free part of the sleeve, and is going therefore to tear at least somewhat in the course the extraction process. However, as is illustrated in FIG. 2, pulled fibers 42 are going to be pulled backwards relative to the extraction, that is distally of the probe electrode 16. Therefore, the fibrosis is not likely to create an overthickness or bulk that might block or plug the extraction during the intravenous journey.

Advantageously, the sleeve of the present invention can be formed of a material that is loaded with particles of a radioopaque material. This will allow one to follow the progress of. the extraction process under a suitable imaging device.

The explantation continues until the extraction of the probe is completed. One will note that the structure of the invention allows one to pull out the entire probe, which is a major advantage when the patient is suffering from a generalized infection. On the other hand, no specific tool is required to achieve the extraction, such as a tool for cutting the sheath, or a Cook extractor, etc., which tools are sometimes difficult to introduce in or around the probe.

One skilled in the art will appreciate that the present invention can be practiced by other than the preferred embodiments, which are presented for purposes of illustration and not of limitation. Numerous other modifications may be made and other arrangements may be devised without departing from the spirit and scope of the invention.

We claim:

1. In a probe (10) for an implanted medical device, a distal probe extremity having a distal end and a proximal end, comprising:

a cylindrical body (14);

an electrode (18) supported by the cylindrical body;

an anchorage system having a radially outward orientation; and a deformable sleeve (24) having a part of attachment (26) and a free part (28), the part of attachment being attached to the cylindrical body at the distal extremity of the probe, wherein the free part (28) further comprises a first position in which it extends against the body proximally relative to the part of attachment and supports thereon the anchorage system with the anchorage system in the radially outward orientation.

2. The distal probe extremity of claim 1 wherein the sleeve further comprises a second position that is inside-out relative to the first position, and wherein the free part extends distally relative to the part of attachment and the anchorage system is in a radially inward orientation in the inside-out sleeve.

3. The distal probe extremity of claim 2 wherein the sleeve further comprises a supple material having a hardness adapted to switch the sleeve from the first position to the second position in response to a first force urging the probe distal end in the proximal direction being greater than a second force urging the anchorage system in the distal direction relative to said first force.

4. The distal probe extremity of claim 2, in which the second position of the sleeve further comprises a mechanically stable state.

5. The distal probe extremity of claim 2, in which the sleeve in the second position further comprises an exposed surface having an essentially smooth surface free of salient elements.

6. The distal probe extremity of claim 1, in which the anchorage system further comprises a plurality of anchorage tines (34).

7. The distal probe extremity of claim 6 in which each of said plurality of anchorage tines further comprises a tapered projection having a base cross-sectional area that is greater than a tip cross-sectional area.

8. The distal probe extremity of claim 1, further comprising a single molded element comprising the sleeve and anchorage system.

9. The distal probe extremity of claim 1, in which the part of attachment further comprises an annular part interposed between the electrode and the cylindrical body and a nonannular part adjacent thereto.

10. The distal probe extremity of claim 9 wherein the deformable sleeve in the first position has a sleeve outer diameter, a first inner diameter corresponding to the annular part, and a second inner diameter corresponding to the nonannular part, wherein the first inner diameter is less than the second inner diameter.

11. The distal probe extremity of claim 1, in which the sleeve further comprises a first thickness and a region of reduced thickness (38) relative to the first thickness, said reduced thickness region being disposed between the free part and the attached part.

12. The distal probe extremity of claim 11, wherein the reduced thickness region further comprises a reduction in the range of from 30 to 70% of the first thickness.

13. The distal probe extremity of claim 1, wherein the sleeve further comprises means for forming a hinge between the part of attachment and the free part at the time the sleeve changes from the first position to the second position.

14. The distal probe extremity of claim 1, further comprising an insulating sheath (12) extended over the cylindrical body wherein the free part of the sleeve, in the first position, further comprises a length sufficient to cover the cylindrical body and to overlap a portion of the insulating sheath.

15. The distal probe extremity of claim 14 wherein the sleeve length is sufficient to cover entirely the cylindrical body.

16. The distal probe extremity of claim 14 wherein the sleeve overlaps the portion of the insulating sheath in tight touching contact.

17. The distal probe extremity of claim 1, further comprising a lubricating agent interposed between the cylindrical body and the free part of the sleeve in the first position.

18. The distal probe extremity of claim 1, in which the sleeve further comprises a radio-opaque material.

* * * * *